United States Patent
Crabe et al.

(10) Patent No.: US 11,266,667 B2
(45) Date of Patent: Mar. 8, 2022

(54) ABX196 FOR USE IN THE TREATMENT OF BLADDER CANCER

(71) Applicant: ABIVAX, Paris (FR)

(72) Inventors: Sandrine Crabe, Saint-Gély-du-Fesc (FR); Didier Scherrer, Castelnau le Lez (FR); Hartmut Ehrlich, Paris (FR); Philippe Pouletty, Paris (FR)

(73) Assignee: ABIVAX, Paris (FR)

( * ) Notice: Subject to any disclaimer, the term of this patent is extended or adjusted under 35 U.S.C. 154(b) by 95 days.

(21) Appl. No.: 16/647,379

(22) PCT Filed: Sep. 13, 2018

(86) PCT No.: PCT/EP2018/074778
§ 371 (c)(1),
(2) Date: Mar. 13, 2020

(87) PCT Pub. No.: WO2019/053142
PCT Pub. Date: Mar. 21, 2019

(65) Prior Publication Data
US 2020/0230163 A1   Jul. 23, 2020

(30) Foreign Application Priority Data
Sep. 13, 2017 (EP) .................... 17306182

(51) Int. Cl.
*A61K 31/7032* (2006.01)
*A61P 35/00* (2006.01)

(52) U.S. Cl.
CPC .......... *A61K 31/7032* (2013.01); *A61P 35/00* (2018.01)

(58) Field of Classification Search
CPC ............................ A61K 31/7032; A61P 35/00
See application file for complete search history.

(56) References Cited

FOREIGN PATENT DOCUMENTS

| WO | 2009/101475 A2 | 8/2009 |
| WO | 2010/040710 A1 | 4/2010 |
| WO | 2018050782 A1 | 3/2018 |

OTHER PUBLICATIONS

Chung, P et al., Urologic Oncology: Seminars and Original Investigations, "Long-term outcome of radiation-based conservation therapy for invasive bladder cancer", 2007, vol. 25, pp. 303-309 (Year: 2007).*
Higuchi, T. et al., Cancer Immunol Immunother, "A possible mechanism of intravesical BCG therapy for human bladder carcinoma: involvement of innate effector cells for the inhibition of tumor growth", 2009, vol. 58, pp. 1245-1255 (Year: 2009).*
Naoe, M. et al., International Journal of Urology, "Bacillus Calmette-Guerin-pulsed dendritic cells stimulate natural killer T cells and gamma-delta T cells", 2007, vol. 14, pp. 532-538 (Year: 2007).*
Mitsuhashi, M. et al., Asian Pacific Journal of Cancer Prevention, "No Inhibition of Urinary Bladder Carcinogenesis in Rats with Intravesical Instillation of alpha-Galactosylceramide", 2003, vol. 4, pp. 45-50 (Year: 2003).*
Internatioanl Search Report and Written Opinion from International Application No. PCT/EP2018/074778, dated Dec. 20, 2018.
Extended European Search Report from European Application No. 17306182.1, dated Mar. 6, 2018.
Tefit et al., "Efficacy of ABX196, a new NKT agonist, in prophylactic human vaccination", Vaccine, Elsevier, Amsterdam, vol. 32, No. 46, Sep. 13, 2014 (Sep. 13, 2017), pp. 6138-6145.

* cited by examiner

*Primary Examiner* — Bahar Craigo
(74) *Attorney, Agent, or Firm* — Merchant & Gould P.C.

(57) ABSTRACT

The compound ABX196 and pharmaceutical compositions including ABX196 are used in the treatment of bladder cancer.

8 Claims, 2 Drawing Sheets

ABX196 FOR USE IN THE TREATMENT OF BLADDER CANCER

This application is a National Stage Application of International Application No. PCT/EP2018/074778, filed Sep. 13, 2018, which claims benefit of Ser. No. 17/306,182.1, filed Sep. 13, 2017 in Europe and which applications are incorporated herein by reference. To the extent appropriate, a claim of priority is made to each of the above-disclosed applications.

The present invention concerns the compound ABX196 and pharmaceutical compositions comprising it, for use in the treatment of bladder cancer.

Cancer is a leading cause of mortality, despite years of research and treatment advances. In particular, bladder cancer is one of the most common cancers among men. In 2014, there were an estimated 696,440 people living with bladder cancer in the United-States.

The bladder is a hollow organ in the lower part of the abdomen that stores urine until it is passed out of the body. In bladder cancer, malignant (tumoral) cells form in the tissues of the bladder. Signs and symptoms of bladder cancer include blood in the urine (hematuria), pain during urination, frequent urination and lower back pain. It is known that smoking and frequent bladder infections can affect the risk of bladder cancer.

Diagnosis is typically made by cystoscopy with tissue biopsies.

The most common type of bladder cancer is transitional cell carcinoma which represents 90% of the bladder cancers and affects urothelial cells that line the inside of the bladder. Urothelial cells are transitional cells, which are able to change shape and stretch when the bladder is full. This type of cancer is also called urothelial carcinoma. Other types of bladder cancer include squamous cell carcinoma (cancer that begins in thin, flat cells lining the bladder) and adenocarcinoma (cancer that begins in cells that make and release mucus and other fluids).

Treatment of bladder cancer depends on the stage of the cancer. It may include surgery, radiation therapy, chemotherapy, immunotherapy, or their combinations.

There are currently two types of chemotherapy that may be used to treat bladder cancer: the intravesical or the systemic chemotherapy.

In intravesical chemotherapy, drugs are delivered into the bladder through a catheter that has been inserted through the urethra. Local treatment only destroys superficial tumor cells that come in contact with the chemotherapeutic composition. Systemic chemotherapy is usually given intravenously or orally. The most common chemotherapy regimens for bladder cancer are combination therapies such as:
- cisplatin and gemcitabine;
- carboplatin and gemcitabine;
- MVAC therapy, which combines 4 drugs: methotrexate, vinblastine, doxorubicin, and cisplatin.

The standard immunotherapy for bladder cancer is a live attenuated strain of *Mycobacterium bovis* called *Bacillus Calmette-Guerin* (BCG). BCG is placed directly into the bladder through a catheter. BCG attaches to the inside lining of the bladder and stimulates the immune system to destroy the tumor.

However, there is still an important need for novel bladder cancer therapies, in particular chemotherapy and/or immunotherapy.

In particular, there is a need for an improved chemotherapy for the treatment of bladder cancer.

An aim of the present invention is to provide a treatment of bladder cancer, more particularly of bladder transitional cell carcinoma.

An aim of the present invention is to provide an antitumor compound, useful in the treatment of bladder cancer.

Another aim of the present invention is to provide an efficient treatment of bladder cancer, in particular to provide a treatment which decreases the tumor volume.

An aim of the present invention is to provide a treatment of bladder cancer which is not a combination of chemotherapeutic and/or immunotherapeutic agents.

An aim of the present invention is to provide a pharmaceutical composition, useful in the treatment of bladder cancer, alone or in combination with surgery and/or radiotherapy.

The present invention thus relates to a compound ABX196 having the following formula (I):

or one of its pharmaceutically acceptable salts, for use in a method for the treatment of bladder cancer.

More particularly, the present invention relates to a compound ABX196 of formula (I):

or one of its pharmaceutically acceptable salts, for use in a method for the treatment of bladder cancer, wherein said method does not comprise the administration of a further chemotherapeutic agent and/or an immunotherapeutic agent and/or an antigen.

The inventors surprisingly found that the specific NKT agonist, namely the α-galactosylceramide derivative ABX196 of formula (I)

has an antitumor activity against bladder cancer, especially when used alone.

By "used alone", it may be meant that ABX196 is not used in combination with a further chemotherapeutic agent and/or an immunotherapeutic agent and/or an antigen.

More particularly, the compound ABX196 surprisingly allows the decrease or reduction of the bladder tumor volume when used alone. This antitumor activity, obtained without the use of a further chemotherapeutic and/or immunotherapeutic agent and/or antigen is of great interest. In particular, the side effects of another chemotherapeutic and/or immunotherapeutic agent(s) can be avoided with such a treatment. The tolerance and observance of the treatment by the patients may thus be improved.

DETAILED DESCRIPTION

ABX196

The compound ABX196, of formula (I)

used according to the invention, is an α-galactosylceramide derivative which is known to stimulate NKT (Natural Killer T) cells. According to the present invention, the compound ABX196 also refers to one of its pharmaceutically acceptable salts. The term "pharmaceutically acceptable salts" refers to salts which retain the biological effectiveness and properties of ABX196 and which are not biologically or otherwise undesirable. For a review of pharmaceutically acceptable salts see Berge, et al. ((1977) J. Pharm. Sd, vol. 66, 1).

As explained above, according to the present invention, ABX196 may be used alone in the treatment of bladder cancer. By "alone", it may be meant that no further chemotherapeutic agent and/or immunotherapeutic agent and/or antigen is used or administered with ABX196 in the treatment of bladder cancer; either simultaneously or separately (i.e. in combination with ABX196). In a particular embodiment, ABX196 is not used as a vaccine adjuvant.

In one embodiment, the pharmaceutical composition according to the invention does not comprise a further chemotherapeutic agent and/or an immunotherapeutic agent and/or an antigen. In another embodiment, said pharmaceutical composition does not comprise or is not a vaccine composition.

Nevertheless, ABX196 may be used in combination with surgery and/or radiotherapy in the treatment of bladder cancer.

Chemotherapeutic Agents

As used herein, the term "chemotherapeutic agent" refers to any cell growth inhibitory compound or cytotoxic compound used in anticancerous chemotherapy, and which is different from ABX196 as defined above.

Such chemotherapeutic agents are well-known from the skilled person and include for example:
  alkylating agents, including nitrogen mustards such as cyclophosphamide, ifosfamide, mechlorethamine, chlorambucil and melphalan; ethyleneamines and methylmelamines such as thiotepa; methylhydrazine derivatives such as procarbazine; alkylsulfonates such as busulfan; nitrosoureas such as carmustine or lomustine; triazenes such as dacarbazine and temozolomide; platinum coordination complexes such as cisplatin, carboplatin and oxaliplatin;
  antimetabolites, including folic acid analogs such as methotrexate; pyrimidine analogs such as fluorouracil, cytarabine, gemcitabine and capecitabine; purine analogs such as mercaptopurine, pentostatin, cladribine and fludarabine;
  vinca alkaloids such as vinblastine, vinorelbine and vincristine;
  taxanes such as paclitaxel and docetaxel;
  epipodophyllotoxins such as etoposide and teniposide;
  camptothecins such as topotecan and irinotecan;
  anticancer antibiotics such as dactinomycin, daunorubicin, doxorubicin, plicomycin and epirubicin;
  anthracenediones such as mitoxantrone, mitomycin and bleomycin;
  mitotic inhibitors such as dolastatins;
  enzymes such as L-asparaginase;
  substituted ureas such as hydroxyurea;
  differentiating agents such as tretinoin;
  protein kinase inhibitors such as imatinib or bryostatin;
  proteasome inhibitors such as gefitinib and bortezomib;
    hormones and antagonists, including adrenocortical suppressants such as aminoglutethimide; adrenocorticosteroids such as prednisone; progestins such as megestrol acetate and medroxyprogesterone; estrogens such as diethylstilbestrol; anti-estrogens such as tamoxifen, idoxifene, droloxifene, zindoxifene, trioxifene, ICI 182,780, EM-800 and toremifene; aromatase inhibitors such as anastrozole, letrozole and exemestane; androgens such as testosterone propionate; anti-androgens such as flutamide; and gonadotropin-releasing agents such as leuprolide.

By "chemotherapeutic agent" it may be meant a compound which is selected from the group consisting of doxorubicin, cyclophosphamide, epirubicin, idarubicin, mitoxantrone and oxaliplatin.

In a preferred embodiment, ABX196 is thus not used in combination with doxorubicin in the treatment of bladder cancer as defined above. In another preferred embodiment, ABX196 is not used in combination with a chemotherapeutic agent chosen among the group consisting of:
  cisplatin, carboplatin, gemcitabine, methotrexate, vinblastine, and doxorubicin in the treatment of bladder cancer as defined above.

The term "chemotherapeutic agent" may refer to a compound formulated in a pharmaceutical composition, which may further comprise pharmaceutically acceptable excipients.

Immunotherapeutic Agents

As used herein, the term "immunotherapeutic agent" refers to an anticancerous agent, which mediates antineoplastic effects by initiating a novel or boosting an existing immune response against cancerous cells, such as antibodies or lymphocytes targeting a tumor antigen, and which is different from ABX196 as defined above.

The immunotherapeutic agent may be classified as "active" or "passive" based on its ability to (re-)activate the host immune system against malignant cells.

An "antibody" may be a natural or conventional antibody in which two heavy chains are linked to each other by disulfide bonds and each heavy chain is linked to a light chain by a disulfide bond. As used herein, the term "antibody" denotes conventional antibodies and fragments thereof, as well as single domain antibodies and fragments thereof, in particular variable heavy chain of single domain antibodies, and chimeric, humanized, bispecific or multispecific antibodies.

As used herein, antibodies also include "single domain antibodies" which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains, such as those produced by *Camelidae* species, for example camel, dromedary, llama, alpaca and guanaco.

The variable heavy chain of these single domain antibodies devoid of light chains are known in the art as "VHH" or "nanobody". Similar to conventional VH domains, VHHs contain four FRs and three CDRs.

The term "monoclonal antibody" or "mAb" as used herein refers to an antibody molecule of a single amino acid composition that is directed against a specific antigen.

A monoclonal antibody may be produced by a single clone of B cells or hybridoma, but may also be recombinant, i.e. produced by protein engineering.

The term "chimeric antibody" refers to an engineered antibody which contains one or more region(s) from one antibody and one or more regions from one or more other antibody(ies). In particular a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin.

The term "humanized antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

"Fragments" of (conventional) antibodies comprise a portion of an intact antibody, in particular the antigen binding region or variable region of the intact antibody. Examples of antibody fragments include Fv, Fab, F(ab')$_2$, Fab', dsFv, (dsFv)$_2$, scFv, sc(Fv)$_2$, diabodies, bispecific and multispecific antibodies formed from antibody fragments. A fragment of a conventional antibody may also be a single domain antibody, such as a heavy chain antibody or VHH The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 Da and antigen binding activity, which is slightly larger than the Fab bound via a disulfide bond of the hinge region, among fragments obtained by treating IgG with a protease, pepsin.

The term "Fab" refers to an antibody fragment having a molecular weight of about 50,000 Da and antigen binding activity, which is obtained by cutting a disulfide bond of the hinge region of the F(ab')$_2$ fragment.

A single chain Fv ("scFv") polypeptide is a covalently linked VH::VL heterodimer which is usually expressed from a gene fusion including VH and VL encoding genes linked by a peptide-encoding linker. The human scFv fragment includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)$_2$.

"dsFv" is a VH::VL heterodimer stabilised by a disulphide bond.

"(dsFv)$_2$" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "immunotherapeutic agent" it may be meant a monoclonal antibody or a fragment thereof, in particular a fragment selected from the group consisting of Fv, Fab, F(ab')$_2$, Fab', dsFv, (dsFv)$_2$, scFv, sc(Fv)$_2$, diabodies and VHH.

By "immunotherapeutic agent" it may be preferably meant a monoclonal antibody.

The immunotherapeutic agent may be an antibody, in particular a monoclonal antibody, specific of a tumor antigen selected from the group consisting of Her2/neu, EGFR, VEGF, CD20, CD52, CD33, TACE, cathepsin S, uPA, uPAR, PD-1, Glypican-3, claudin-3, claudin-4, BMCA and CTLA4. The immunotherapeutic agent may be an antibody, in particular a monoclonal antibody, specific of PD-1. In one embodiment, the immunotherapeutic agent is an antibody selected from the group consisting of: anti-PD-1, anti-CTLA-4, anti-PD-L1, anti-GITR, anti-CD38, anti-4-1BB, anti-OX40, anti-LAG3 and anti-TIM-3. The immunotherapeutic agent may particularly be a monoclonal anti-PD1 antibody.

Examples of monoclonal antibodies specific of tumor antigens are well-known from the skilled person and include rituximab, trastuzumab (Herceptin), alemtuzumab, cetuximab, panitumumab, bevacizumab, ipilimumab, nivolumab (also known as MBS-936558, MDX-1106 or ONO-4538 anti-PD-1 antibody), pembrolizumab (also known as MK-3475 anti-PD-1 antibody), pidilizumab (also known as CT-011 anti-PD-1 antibody), BMS-936559 anti-PD-L1 antibody, MPDL3280A anti-PD-L1 antibody, MEDI4736 anti-PD-L1 antibody, MSB0010718C anti-PD-L1 antibody, D1(A12) anti-TACE antibody, A9 anti-TACE antibody, Fsn0503h anti-cathepsin S antibody, ATN-658 anti-uPAR antibody, or the J6M0 anti-BMCA antibody.

By "immunotherapeutic agent" it may be meant a compound selected from the group consisting of nivolumab, pembrolizumab and pidilizumab.

In a preferred embodiment, ABX196 is thus not used in combination with a monoclonal anti-PD1 antibody or BCG, preferably monoclonal anti-PD1 antibody, in the treatment of bladder cancer as defined above.

The immunotherapeutic agent may also be a conjugate comprising a monoclonal antibody as defined above and a chemotherapeutic agent as defined in the section "Chemotherapeutic agent" above.

In another embodiment, the immunotherapeutic agent is an adoptively transferred T cell.

The term "adoptive cell transfer" refers to a variant of cell-based anticancer immunotherapy that generally involves (1) the collection of circulating or tumor-infiltrating lymphocytes, (2) their selection/modification/expansion/activation ex vivo and (3) their (re)administration to patients, most often after lymphodepleting pre-conditioning and in combination with immunostimulatory agents.

The immunotherapeutic agent may be formulated in a pharmaceutical composition, which may further comprise pharmaceutically acceptable excipients, as defined below.

Antigen

The term "antigen" as used herein refers to a molecule that is capable of being bound by an antibody or an antibody-like binding protein. The term further refers to a molecule that is capable of being used in an animal to produce antibodies that are capable of binding to an epitope of that antigen. A target antigen may have one or more epitopes.

Preferably, by "antigen" is meant a "tumor antigen" which is an antigen expressed exclusively on, associated with, or over-expressed in tumor tissue. Exemplary tumor antigens include, but are not limited to, 5-α-reductase, α-fetoprotein (AFP), AM-1, APC, APRIL, B melanoma antigen gene (BAGE), β-catenin, Bcl12, Bcr-Abl, Brachyury, CA-125, caspase-8 (CASP-8, also known as FLICE), Cathepsin S, CD19, CD20, CD21/complement receptor 2 (CR2), CD22/BL-CAM, CD23/FcεRII, CD33, CD35/complement receptor 1 (CRT), CD44/PGP-1, CD45/leucocyte common antigen (LCA), CD46/membrane cofactor protein (MCP), CD52/CAM PATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene (DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc:R$_1$Man(α1-6)R$_2$[GlcNAc to Man(α1-6)]β1,6-N-acetylglucosaminyltransferase V (GnTV), GP1, gp100/Pme1-17, gp-100-in4, gp15, gp75/tyrosine-related protein-1 (gp75/TRP-1), human chorionic gonadotropin (hCG), heparanase, Her2/neu, EGFR, human mammary tumor virus (HMTV), 70 kD heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding family (MAGE-family, including at least MAGE-1, MAGE-2, MAGE-3, and MAGE-4), mammaglobin, MAP17, Melan-A/melanoma antigen recognized by T-cells-1 (MART-1), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor (PDGF), PRAME, probasin, progenipoietin, prostate-specific antigen (PSA), prostate-specific membrane antigen (PSMA), prostatic acid phosphatase (PAP), RAGE-1, Rb, RCAS1, SART-1, SSX-family, STAT3, STn, TAG-72, transforming growth factor-α (TGF-α), transforming growth factor-β (TGF-β), uPA, uPAR, TNF-α Converting Enzyme (TACE), Thymosin-β-15, tumor necrosis factor-α (TNF-α), TP1, TRP-2, tyrosinase, vascular endothelial growth factor (VEGF), ZAG, p16INK4, PD-1, PD-L1, PD-L2, glypican-3, claudin-3, claudin-4, BMCA, and glutathione-S-transferase (GST).

Preferably, the compound ABX196 is used alone, not in combination with an antigen, preferably not in combination with a tumor antigen such as an antigen expressed by melanoma cancer cells, for example TRP-2.

Pharmaceutical Composition

The invention also relates to a pharmaceutical composition comprising the compound ABX196 of formula (I):

(I)

for use as defined above, and one or more pharmaceutically acceptable excipient(s).

The pharmaceutical composition used in the context of the invention may further comprise pharmaceutically acceptable excipients.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical composition used in the context of the invention may be administered by any suitable route well-known from the skilled person. As appreciated by skilled artisans, the pharmaceutical composition can be suitably formulated to be compatible with the intended route of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, intraocular and rectal administration.

Preferably, ABX196 or the pharmaceutical composition used in the context of the invention is administered intravenously, intravesically (i.e locally in the bladder) or intratumorally.

In one embodiment, ABX196 or the pharmaceutical composition used in the context of the invention is administered intravesically (i.e. locally in the bladder) or intravenously.

ABX 196 or the pharmaceutical composition used in the context of the invention may be administered once to a patient in need thereof, or several times.

The pharmaceutical composition used in the context of the invention may be delivered in doses of compound ABX196 of at least 0.2 μg/patient. In one embodiment, the pharmaceutical composition used in the context of the invention may be delivered in doses of compound ABX196 of at least 3 ng/kg, for example between 3 ng/kg and 5 ng/kg. Effective doses will also vary depending on route of administration.

Method of Treatment

The present invention also concerns a method for treating bladder cancer as defined above, comprising the administration in a patient in need thereof of a therapeutically effective amount of a compound ABX196 of formula (I) as defined above.

In a particular embodiment, said method does not comprise the administration of a further chemotherapeutic agent and/or immunotherapeutic agent and/or antigen as defined above.

The present invention also concerns the use of a compound ABX196 of formula (I)

for the manufacture of a medicament for the treatment of bladder cancer. In a particular embodiment, said use does not comprise the administration of a further chemotherapeutic agent and/or immunotherapeutic agent and/or antigen as defined above.

Bladder Cancer

In one embodiment, the bladder cancer is selected among the group consisting of: bladder transitional cell carcinoma, bladder squamous cell carcinoma, and bladder adenocarcinoma; preferably bladder transitional cell carcinoma.

Transitional cell carcinoma may be low-grade or high-grade. By "low-grade transitional cell carcinoma", it may be meant a bladder cancer which relapses after treatment (re-current cancer). By "high-grade transitional cell carcinoma", it may be meant a bladder cancer which relapses after treatment and spreads into the muscle layer of the bladder to other parts of the body, and eventually to lymph nodes.

In another embodiment, the bladder cancer is a superficial or an invasive cancer.

By "superficial bladder cancer" is meant when bladder cancer is in the lining of the bladder.

By "invasive or infiltrative cancer" is meant a bladder cancer that has spread through the lining of the bladder and invades the muscle wall of the bladder and/or has spread to nearby organs and/or lymph nodes.

In a particular embodiment, the bladder cancer is selected from bladder cancers having one of the following stages:

Stage 0a: This cancer stage is only found on the surface of the inner lining of the bladder. This type of bladder cancer is also called noninvasive papillary urothelial carcinoma (Ta, N0, M0).

Stage 0 is: This stage of cancer, also known as flat, is found only on the inner lining of the bladder and is high-graded (Tis, N0, M0).

Stage I: The cancer has grown through the inner lining of the bladder into the lamina propria (T1, N0, M0).

Stage II: The cancer has spread into the thick muscle wall of the bladder. It is also called invasive cancer or muscle-invasive cancer (T2, N0, M0).

Stage III: The cancer has spread throughout the muscle wall to the fatty layer of tissue surrounding the bladder. It may also have spread to the prostate in a man or the uterus and vagina in a woman (T3 or T4a, N0, M0).

Stage IV: Any of these conditions:
The tumor has spread to the pelvic wall or the abdominal wall but not to the lymph nodes or other parts of the body (T4b, N0, M0).
The tumor has spread to one or more regional lymph nodes but not to other parts of the body (any T, N1-3, M0).
The tumor may or may not have spread to the lymph nodes but has spread to other parts of the body (any T, any N, M1).

In a particular embodiment, according to the use of the invention, the bladder tumor volume after treatment with the compound ABX196 is decreased compared to the bladder tumor volume before treatment.

In another particular embodiment, according to the use of the invention, the bladder tumor volume after treatment with the compound ABX196 is decreased compared to the bladder tumor volume after treatment with another chemotherapeutic agent and/or immunotherapeutic agent and/or antigen, preferably another immunotherapeutic agent such as anti-PD1 antibody.

In another particular embodiment, according to the use of the invention, the bladder tumor volume after treatment with the compound ABX196 is decreased or is the same as the bladder tumor volume after treatment with BCG, preferably for the same duration of treatment.

In one embodiment, according to the use of the invention, the bladder tumor volume after treatment with the compound ABX196 is decreased compared to the bladder tumor volume after treatment with a control. Preferably, said treatment with a control refers to a treatment with a vehicle (i.e. a composition comprising no antitumoral agent), an immunotherapeutic agent, or a chemotherapeutic agent administered to the tumor bladder, preferably during the same duration of treatment. In one embodiment, "bladder tumor volume" refers to the mean "bladder tumor volume".

In one embodiment, the T/C ratio (%) of the compound ABX196 is comprised between 50% and 60%, for example is of about 54%, and preferably inferior or equal to 42%.

The percent treated/control ratio (T/C (%)) may be calculated by dividing the median treated tumor volume by the median control tumor volume and multiplying it by 100. For example, the median treated tumor volume is obtained following the administration of ABX196, and the median control tumor volume is obtained following the administration of the vehicle of ABX196, said tumor volumes being assessed at the same time.

In a particular embodiment, said treatment of bladder cancer further comprises surgery and/or radiation therapy.

By "surgery", it may be meant the transurethral resection of the bladder tumor (removal of the tumor only) or the partial or complete cystectomy (removal of a part or of the whole bladder).

By "radiation therapy" it may be meant the use of high-energy x-rays or other particles to destroy cancer cells. Radiation therapy may be given using implants. A radiation therapy regimen usually consists of a specific number of treatments given over a set period of time.

All the above-mentioned embodiments apply to the use of ABX196 as defined above, or to the use of the pharmaceutical composition as defined above or to the method of treatment according to the invention.

According to the invention, the term "patient", "subject" or "subject in need thereof" is intended for a human or non-human mammal affected or likely to be affected with a bladder cancer.

In the context of the invention, the term "treating" or "treatment" means reversing, alleviating, inhibiting the progress of, or preventing the disorder or condition to which such term applies, or one or more symptoms of such disorder or condition.

By a "therapeutically effective amount" of a compound of the invention is meant a sufficient amount of the compound ABX196 to treat a bladder cancer, (for example, to limit growth or to slow or block tumor metastasis) at a reasonable benefit/risk ratio applicable to any medical treatment. It will be understood, however, that the total daily usage of the compounds of the present invention will be decided by the attending physician within the scope of sound medical judgment. The specific therapeutically effective dose level for any particular subject will depend upon a variety of factors including the disorder being treating and the severity of the disorder, activity of the specific compounds employed, the specific combinations employed, the age, body weight, general health, sex and diet of the subject, the time of administration, route of administration and rate of excretion of the specific compounds employed, the duration of the treatment, drugs used in combination or coincidental with the specific compounds employed, and like factors well known in the medical arts. For example, it is well within the skill of the art to start doses of the compounds at levels lower than those required to achieve the desired therapeutic effect and to gradually increase the dosage until the desired effect is achieved.

More particularly, the term "treatment of bladder cancer" as used herein includes at least one of the following features: alleviation of the symptoms associated with the bladder cancer, a reduction in the extent of the cancerous tumor (e.g. a reduction in tumor growth), a stabilization of the state of the cancerous tumor (e.g. an inhibition of tumor growth), a prevention of further spread of the cancer (e.g. a metastasis), a prevention of the occurrence or recurrence of a cancer, a delaying or retardation of the progression of the cancer (e.g. a reduction in tumor growth) or an improvement in the state of the cancer (e.g. a reduction in tumor size or volume).

The present invention will be further illustrated by the figures and examples below.

EXAMPLES

Example 1: Anti-Tumoral Activity of the Compound ABX196

Study Aims

The aim of this study is to determine the anti-tumoral activity of ABX196 or of anti-PD-1 antibody, administered systemically alone, in MBT2 syngeneic ectotopic models and in particular, to evaluate the capacity of these agents to treat established sub-cutaneous tumors.

Materials and Methods

1. Products

Anti-PD-1 antibody (ref.: BE0146, BioXcell; clone: RMP1-14, reactivity: mouse; isotype: Rat IgG2a; storage conditions: +4° C.). Anti-PD-1 antibody is prepared in phosphate buffered saline (PBS) or other suitable vehicle according to manufacturer's recommendation. The anti-PD-1 antibody is administered at the dose of 10 mg/kg. Anti-PD-1 antibody is injected into the peritoneal cavity of mice (Intraperitoneally, IP). Anti-PD-1 antibody is administered at a dose volume of 10 mL/kg/adm.

ABX196 is provided as a solution at 250 μg/mL and is administered at the dose of 100 ng per mouse. ABX196 is injected by the intravenous route in the caudal vein of mice (IV, bolus). ABX196 is administered at a fixed dose volume of 100 μL (i.e. approximately 5 mL/kg/adm. for one mouse weighing 20 g).

2. Cancer Cell Line

TABLE 1

| Cancer cell line | | | |
|---|---|---|---|
| Cell line | Type | Specie | Origin |
| MBT-2 | Bladder carcinoma | mouse | ATCC[a] |

The murine MBT-2 cell line was derived from a carcinogen-induced bladder tumor in C3H/HeJ mice. The MBT-2 cell line was obtained from Dr Cozzi, Memorial Sloan Kettering Cancer Center (New York, USA).

Tumor cells are grown as monolayer at 37° C. in a humidified atmosphere (5% $CO_2$, 95% air). The culture medium is RPMI 1640 containing 2 mM L-glutamine (ref: BE12-702F, Lonza, Verviers, Belgium) supplemented with 10% fetal bovine serum (ref: 3302, Lonza). Tumor cells are adherent to plastic flasks. For experimental use, tumor cells are detached from the culture flask by a 5-minutes treatment with trypsin-versene (ref: BE02-007E, Lonza), in Hanks' medium without calcium or magnesium (ref: BE10-543F, Lonza) and neutralized by addition of complete culture medium.

The cells are counted and their viability are assessed by 0.25% trypan blue exclusion assay.

3. Animals 68 (sixty-eight) healthy female C3H/HeJ (C3H/HeOuJ) mice, 6-7 weeks old, are obtained from The Jackson Laboratory (Bar Harbor, Me.) for the MBT-2 model.

4. Induction MBT-2 Tumors in Animals

MBT-2 tumors are induced by subcutaneous injection of $1 \times 10^6$ cells in 200 µL of RPMI 1640 into the right flank of the sixty-eight female animals.

5. Treatment Schedule

The treatment starts when the tumors reach a mean volume of 80-120 $mm^3$ (day 13 in this experiment). The sixty-eight mice for the MBT-2 model are randomized according to their individual tumor volume into 4 groups each (one not shown) of 12 animals using Vivo Manager® software (Biosystemes, Couternon, France). A statistical test (analysis of variance, ANOVA) is performed to test for homogeneity between groups. The treatment schedule was chosen as follows:

Animals from group 1 receive an IV injection of ABX196 vehicle and an IP injection of anti-PD-1 antibody vehicle, Animals from group 2 receive an IV injection of 100 ng of ABX196, Animals from group 3 receive twice weekly administrations of anti-PD-1 antibody, The treatment schedule is summarized in the table 2 below.

TABLE 2

| Treatment schedule | | | | | |
|---|---|---|---|---|---|
| Group | Number of animals | Treatment | Dose (mg/kg/adm) | Adm. Route | Treatment schedule |
| 1 | 12 | Vehicule ABX196 | — | IV | Q1Dx1 |
|  |  | Vehicule Anti-PD-1 Ab | — | IP | TWx2 |
| 2 | 12 | ABX196 | 100 ng | IV | Q1Dx1 |
| 3 | 12 | Anti-PD-1 Ab | 10 mg/kg | IP | TWx2 |

*:IP injection of anti-PD-1 Ab is initiated after the first IV administration of ABX196 (Concomittant administration) without any delay.

Results

Figure 1:
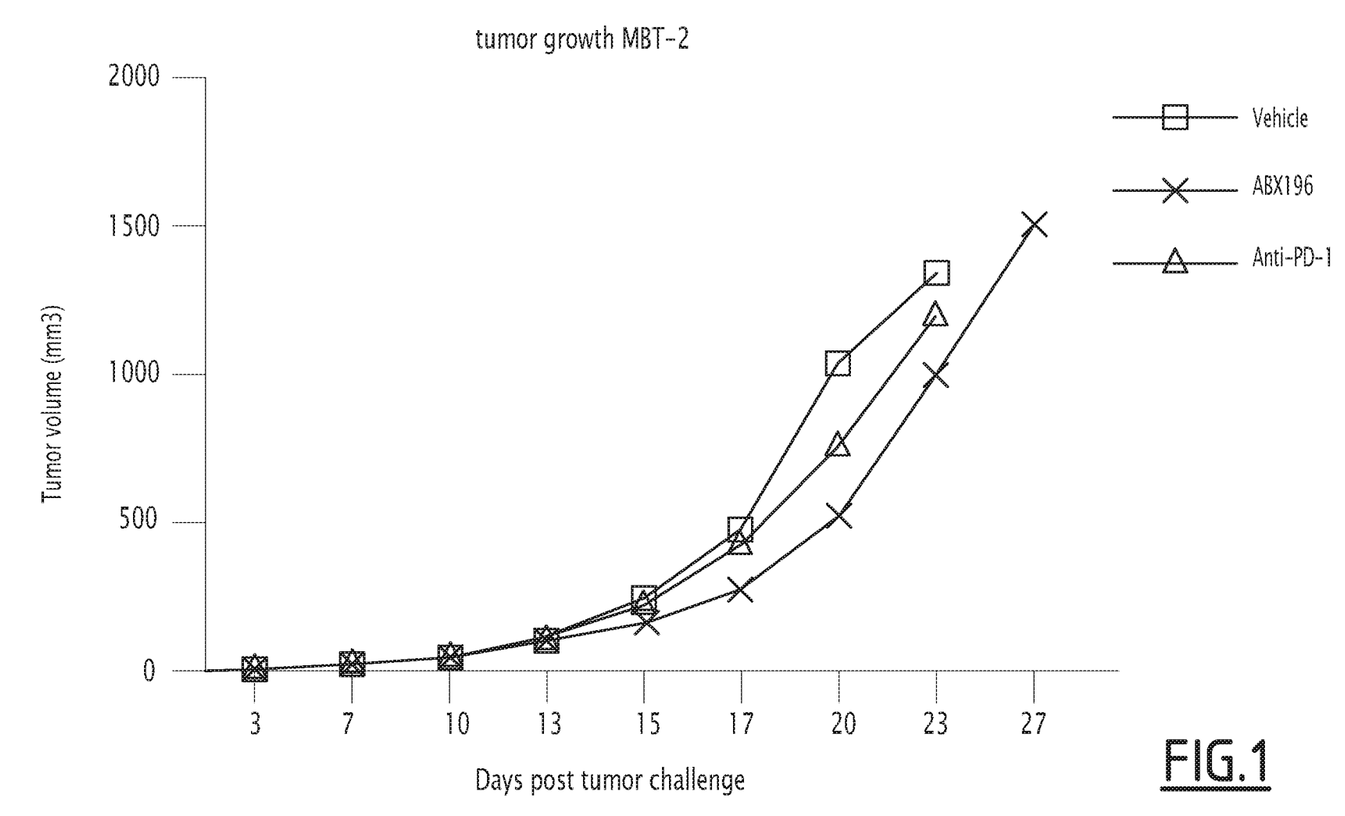
FIG. 1 shows the mean bladder tumor volume in function of the time after tumor induction, depending on the different tested treatments.

1. Tumor Volume:

The results are given in FIG. 1 which shows the mean tumor volume in function of the time after tumor induction (post tumor challenge). These results show that ABX196 reduces more efficiently the tumor volume than anti-PD-1 antibodies.

2. Tumor Growth Inhibition:

The statistical analyses for the tumor growth inhibition are assessed as shown in Table 3 here-below.

TABLE 3

Statistical analyses for tumor growth at day 20 between each group one way ANOVA test; p value = 0,0226 (*); Pair wise Bonferroni's multiple comparison test

|  | Vehicle | ABX196 | Anti-PD-1 |
|---|---|---|---|
| Vehicle |  | * | ns |
| ABX196 | * |  | ns |
| Anti-PD-1 | ns | ns |  |

Ns: non significant; p value < 0.05*

Figure 2:
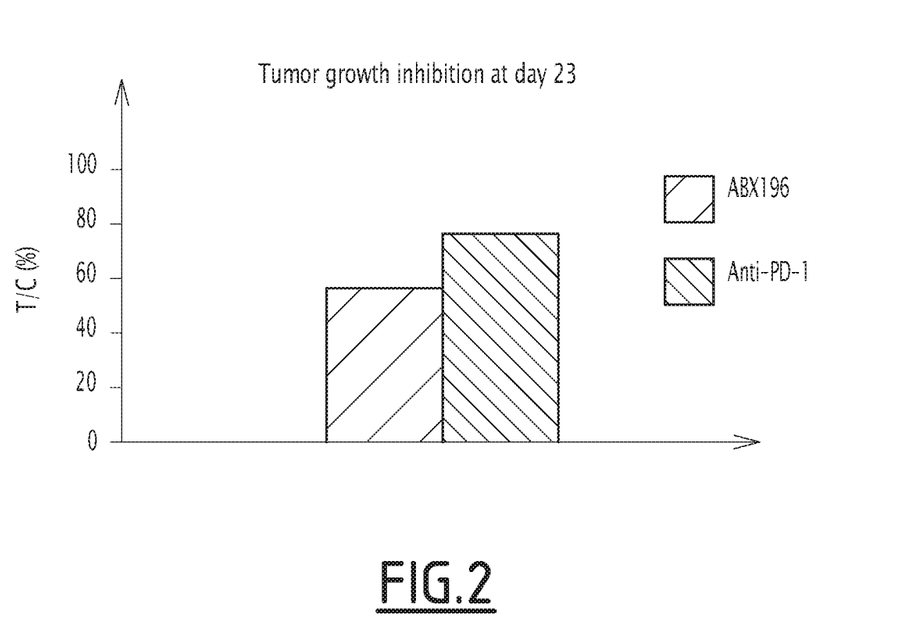
FIG. 2 shows the tumor growth inhibition (T/C %) at day 23 after tumor induction, depending on the different tested treatments.

Tumor growth inhibition (T/C) is defined as the ratio of the median tumor volumes of treated versus control group. The optimal value is the minimal T/C ratio reflecting the maximal tumor growth inhibition achieved. It is observed in FIG. 2 that ABX196 inhibits more efficiently the tumor growth than anti-PD-1 antibodies. The corresponding T/C (%) values are given in the Table 4 below.

TABLE 4

| | T/C (%) values | |
|---|---|---|
|  | ABX196 | Anti-PD-1 |
| T/C (%) | 54 | 93 |

Example 2: Comparison Study with Standard Care for Bladder Cancer

Aim: to compare ABX196 with the BCG vaccine (standard care) in OT model

The protocol steps are:
  In vitro amplification of the MBT-2 tumor cell line;
  Orthotopic injection of tumor cells in mice;
  Randomization of mice based on body weight (4 groups, 12 mice/group);
  Treatment preparation;
  Treatment of the mice groups following the here-below schedule:

| Group | Number of animals | Treatment | Dose (mg/kg/adm) | Adm. Route | Treatment schedule |
|---|---|---|---|---|---|
| 1 | 12 | Non treated | — | — | — |
| 2 | 12 | ABX196 | — | IV | Q1Dx1 |
| 3 | 12 | Anti-PD-1 Ab | 10 | IP | TWx2 |
| 4 | 12 | BCG | 1.35 | Instillation | Q7Dx3 |

Twice weekly monitoring of mice for body weight;

Daily monitoring of mice for behavior and survival; and

Collection of blood (for serum preparation) from all mice 12-18h after the first injection of ABX196.

Example 3: Antitumor Activity Study of ABX196, Anti-PD-1 Targeting Antibodies and BCG in Mice Bearing Orthotopic mbt-2 Tumor Cells 1. Animals and animal care:
105 C3H mice are bought and caged under SPF conditions for 6 weeks.

2. Antitumor Activity Study:
The protocol steps are:
In vitro amplification of the MBT-2 tumor cell line;
Orthotopic injection of tumor cells in the mice;
Randomization of mice based on body weight (7 groups, 12 mice/group, 84 total mice); and
Treatment of the mice following the here-below schedule:

| Group | No. Animals | Treatment | Dose (mg/kg/inj) | Route | Treatment schedule |
|---|---|---|---|---|---|
| 1 | 12 | Non treated | — | — | — |
| 2 | 12 | ABX196 | To Be Determined | IV | Q1Dx1 |
| 3 | 12 | Anti-PD-1 Ab | 10 | IP | TWx2 |
| 4 | 12 | BCG | 1.35 | Instillation | Q7Dx3 |
| 5 | 12 | ABX196 | To Be Determined | IV | Q1Dx1 |
|   |    | Anti-PD-1 Ab | 10 | IP | TWx2 |
| 6 | 12 | ABX196 | To Be Determined | IV | Q10Dx2 |
|   |    | Anti-PD-1 Ab | 10 | IP | TWx2 |
| 7 | 12 | ABX196 | To Be Determined | IV | Q10Dx2 |
|   |    | BCG | 1.35 | Instillation | Q7Dx3 |

*Q1Dx1 = one administration
TWx2 = Twice weekly
Q7Dx3 = 1 injection every 7 days, x3
Q10Dx2 = 2 injections every 10 days

The invention claimed is:

1. A method for treating bladder cancer, comprising administration in a patient in need thereof of a therapeutically effective amount of a compound ABX196 of formula (I):

(I)

or a pharmaceutically acceptable salt of formula (I), without administering a further chemotherapeutic agent, an immunotherapeutic agent, or an antigen.

2. The method according to claim 1, wherein the bladder cancer is selected among the group consisting of: bladder transitional cell carcinoma, bladder squamous cell carcinoma, and bladder adenocarcinoma.

3. The method according to claim 2, wherein the bladder cancer is the bladder transitional cell carcinoma.

4. The method according to claim 1, wherein the bladder cancer is a superficial or an invasive cancer.

5. The method according to claim 1, wherein the compound ABX196 is administered intravesically or intravenously.

6. The method according to claim 1, wherein said method of treatment of bladder cancer further comprises surgery radiation therapy.

7. The method according to claim 1, wherein volume of a bladder tumor is decreased after treatment with the compound ABX196 compared to the tumor volume before treatment.

8. A method for treating bladder cancer, comprising administration in a patient in need thereof of a therapeutically effective amount of a pharmaceutical composition comprising the compound ABX196 of formula (I):

(I)

and one or more pharmaceutically acceptable excipient(s) without administering a further chemotherapeutic agent, an immunotherapeutic agent, or an antigen.

* * * * *